United States Patent
Wack

[11] Patent Number: 6,126,659
[45] Date of Patent: Oct. 3, 2000

[54] IMPACTION INSTRUMENTS

[75] Inventor: Michael A. Wack, Warsaw, Ind.

[73] Assignee: Depuy Orthopaedics, Inc., Warsaw, Ind.

[21] Appl. No.: 09/163,633

[22] Filed: Sep. 30, 1998

[51] Int. Cl.[7] .................................................. A61B 17/56
[52] U.S. Cl. ............................................... 606/60; 623/23
[58] Field of Search ................................ 606/99, 84–86, 606/60–63; 623/22–23, 18–21

[56] References Cited

U.S. PATENT DOCUMENTS

| | | | |
|---|---|---|---|
| 5,019,108 | 5/1991 | Bertin et al. | 623/23 |
| 5,192,283 | 3/1993 | Ling et al. | |
| 5,470,336 | 11/1995 | Ling et al. | |
| 5,507,830 | 4/1996 | DeMane et al. | 623/23 |

FOREIGN PATENT DOCUMENTS

WO 94/17757  8/1994  WIPO ................................ A61F 2/36

*Primary Examiner*—Michael Buiz
*Assistant Examiner*—Jonathan D. Goldberg

[57] ABSTRACT

An instrument and method are provided for compacting bone chips into a prepared metaphyseal portion of a femur, in order to conform the femur to receive a femoral implant stem. The instrument comprises a tamping stem having a shape and size corresponding to the implant stem. The instrument also comprises a plurality of wedge-shaped enlarging portions ranging from largest to smallest. The method involves selecting appropriate sized enlarging portions, attaching the largest wedges to the instrument, placing the instrument into the femur, supplying bone chips, impacting the instrument to compact bone chips, and repeating compaction with successively smaller wedges until the femur is conformed to receive the femoral implant stem. Once inserted into the femur, the distal end of the instrument remains in contact with the diaphysis throughout the bone chip compaction process. Thus, bone chips cannot enter the diaphysis, and the instrument remains in proper alignment throughout the process.

17 Claims, 2 Drawing Sheets

IMPACTION INSTRUMENTS

BACKGROUND OF THE INVENTION

The present invention relates to an instrument and method for compacting bone chips into the prepared metaphyseal portion of a femoral cavity near the proximal end of the femur. Once the bone chips are compacted with this instrument according to this method, the femoral cavity is conformed to receive a femoral implant stem. The instrument and method of the present invention are intended to provide implant support through augmentation of the proximal cortical shell.

As is well known, it is often necessary to replace the femoral portion of a hip joint prothesis. In the course of such revision surgery, the prior prosthesis is removed from the femur. If cement was used in the prior surgery, such cement is also removed. Techniques for removing the prosthesis and cement are known in the art. Often, after removal of the old prosthesis and cement, the resulting femoral cavity is larger than desired. It is known in the art to use crushed bone graft to fill this resulting cavity. U.S. Pat. Nos. 5,047,035, 5,192,283, and 5,470,336 relate to methods and instruments for performing hip prothesis revision surgery using crushed cancellous bone graft to prepare the cavity for receiving a prosthesis. These patents also disclose various techniques for removing the old cement.

The prior art methods of the '035, '283, and '336 patents employ the use of a guidewire which is placed longitudinally in the cavity and extends into the diaphysis. Crushed bone graft is placed in the cavity, a cannulated tamp is positioned over the guidewire, and the tamp is impacted to compact the bone within the cavity. Successively larger tamps may be used until the cavity is the desired size. The result is a cavity sized to receive a layer of cement and the replacement prosthesis. The crushed bone graft material is sufficiently compacted to provide support for the replacement prosthesis.

The prior art references noted above are incorporated herein by reference for purposes of disclosing the concepts, instruments and techniques involved in removing the prior prosthesis and compacting bone chips to provide a cavity prepared to receive a new prosthesis stem.

The instrument and method of the present invention are provided to facilitate the process of compacting bone chip layers in the femoral cavity by using a single impaction stem, the proximal end portion of which is reduced in size in steps to provide a well compacted wall of bone chips accurately shaped to fit the proximal portion of a prosthesis stem. The instrument and method of the current invention also overcomes the need for a guidewire and cannulations.

SUMMARY OF THE INVENTION

The present invention, therefore, is an instrument for compacting bone chips into a prepared metaphyseal portion of a femur conformed to receive a femoral implant stem. The implant stem longitudinally extends from the proximal end of the femur toward the distal end of the femur. The instrument comprises a tamping stem or impaction stem having a proximal end and a distal end and a size and shape corresponding to the implant stem. The instrument further comprises a plurality of enlarging portions to be attached to the impaction stem, the enlarging portions ranging in size from a largest size portion to a smallest size portion such that the bone compaction can be initiated with the largest size and repeated with successively smaller portions, including the smallest portion. The smallest portion may then be removed to finish the bone chip compaction with the impaction stem to provide a cavity conformed to receive an implant stem. Alternatively, it may be possible within the present invention to have the impaction stem with the smallest enlarging portion conform in shape and size to the implant stem.

The enlarging portions may be wedge shaped and provided in pairs to be attached to the proximal end portion of the impaction stem. Each wedge shaped portion tapers downwardly in size from its proximal end to its distal end. The enlarging portions or wedges of a pair may have different sizes and shapes. In accordance with the present invention, the enlarging portions or wedges may be attached to the anterior and posterior sides of the impaction stem, and the anterior and posterior wedges may differ in size and shape to accommodate the desired cavity shape. Each enlarging portion is preferably wedge shaped tapering downwardly in size from its proximal end to its distal end.

The instrument of the present invention may be constructed such that each enlarging portion is provided with a connector portion and the impaction stem would be provided with a mating connector portion. These connector portions preferably may be male and female dovetail slide portions, one on the enlarging portion and one on the impaction stem. The slide portions may extend longitudinally in the proximal-to-distal direction of the stem and the enlarging portions, and the slide portions may be held in rigid contact by a member carried by the handle for the impaction stem.

The distal end of the instrument may be elongated, such that when the instrument is inserted into the femur, the distal end extends into the diaphyseal portion of the femur. Ideally, the distal end of the instrument should remain in contact with the diaphysis throughout the impacting process. In this way, the distal end will prevent bone chips from entering the diaphysis. If the distal end is sufficiently elongated, the instrument may be partially withdrawn to allow replacement of the enlarging portions without disengaging from the diaphysis. This feature also has the benefit of preserving alignment of the instrument within the femur. The instrument may be provided with a plurality of stem extensions which thread into the distal end of the instrument, such that the surgeon may choose a stem extension of the appropriate length.

The present invention also provides a method for compacting bone chips into a prepared metaphyseal portion of a femur to receive a prosthesis stem. The method comprises the steps of providing an impaction stem having a size and shape corresponding to the size and shape of the prosthesis stem to be installed in the femur. A plurality of enlarging portions are provided to be attached to the impaction stem, the enlarging portions ranging in size from a largest size portion to the smallest size portion. The femoral cavity is filled with bone chips. Starting with the largest size portion attached to the impaction stem, a layer of bone chips is compacted within the cavity, with the bone chips lining the exterior wall of the cavity. This step is repeated with successively smaller enlarging portions and finally with the impaction stem itself without any enlarging portions attached, to obtain a cavity lined with compacted bone chips conformed to receive the prosthesis stem. Each enlarging portion may be wedge shaped to be larger at its proximal end than at its distal end. These wedge shaped enlarging portions may be provided in pairs to be attached to the opposite sides of the proximal end of the impaction stem, typically on the anterior and posterior sides of the impaction stem. The attachment of the enlarging portions to the impaction stem may be accomplished by rigid interlocking connector portions extending longitudinally. These connector portions may be held to the connection stem and enlarging portions by means of a handle with a member which holds the connector portions together.

DETAILED DESCRIPTION

Figure 1:
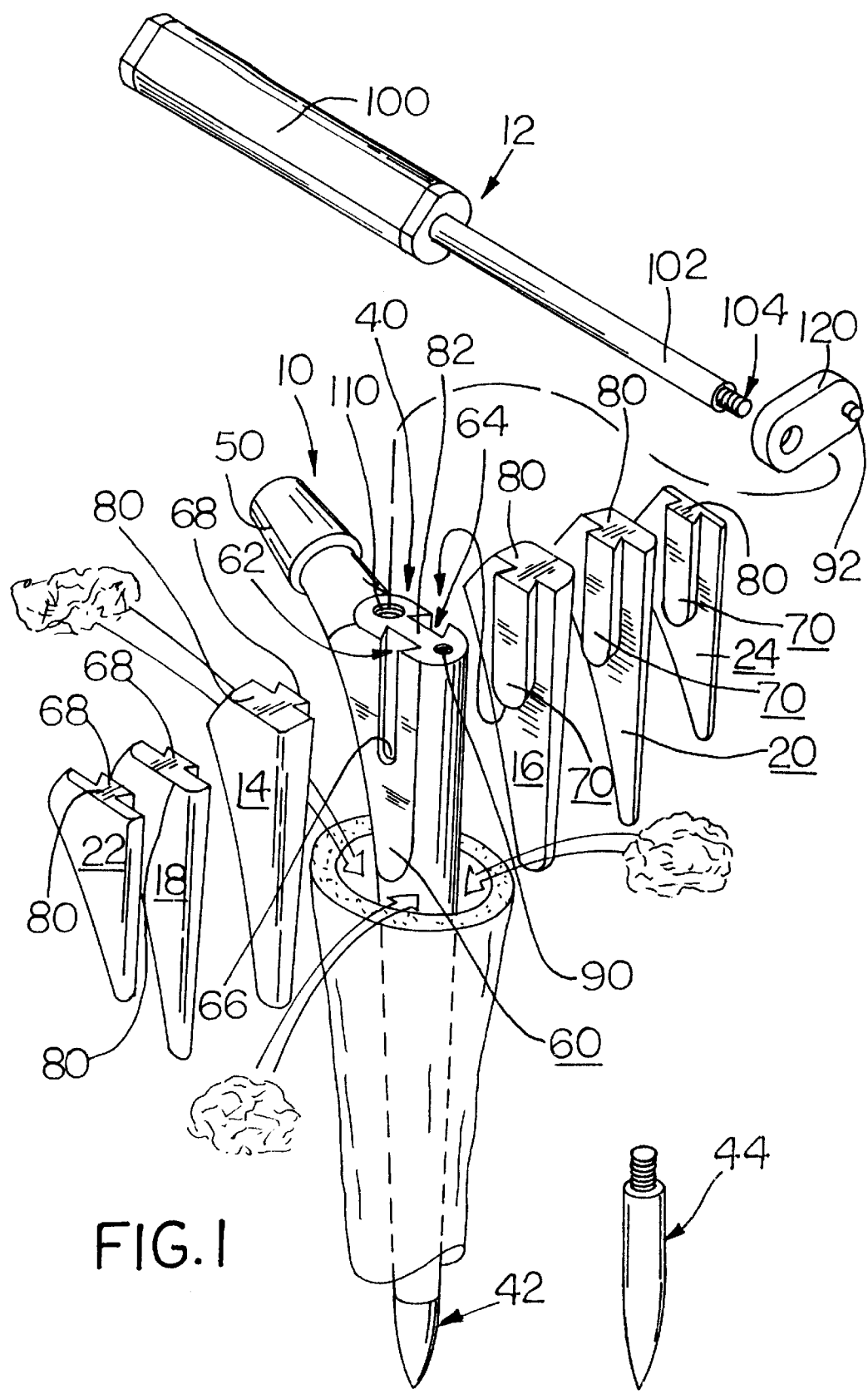
FIG. 1 is an exploded perspective view showing the instrument of the present invention comprising an impaction stem, a plurality of enlarging portions, a handle for use in selectively attaching the enlarging portions to the impaction stem, and a stem extension which can replace the distal end of the impaction stem.

Referring now to FIG. 1, it will be seen that the illustrative instrument of the present invention comprises an impaction stem 10, a handle 12, and a plurality of enlarging portions 14, 16, 18, 20, 22, 24 selectively to be attached to the stem 10. The enlarging portions are illustratively provided in pairs 14, 16 as the largest pair, portions 18 and 20 as the intermediate pair and portions 22, 24 as the smallest pair.

The impaction stem 10 preferably may be formed to have a shape and size equal to that of the prosthesis stem to be implanted. Alternatively, the impaction stem 10 along with the smallest pair of enlarging portions 22, 24 may preferably have a shape and size equal to that of the prosthesis stem. The illustrative stem 10 comprises a proximal end 40 and a distal end 42. It will be appreciated that the stem extends longitudinally in the proximal-distal direction to fit within the intramedullary cavity of the proximal end portion of the femur, a portion of which is represented in the drawings. In the illustrated embodiment, the distal end 42 is threadedly removable, and it may be replaced by stem extensions 44 of varying length. Such stem extensions 44 would accommodate different lengths of the corresponding implant and would keep bone chips from falling into the diaphyseal portion of the femur.

The proximal portion of the stem 10 is formed to have a conventional neck similar to that provided on a prosthesis stem terminating with a tapered trunnion 50 upon which a spherical ball with a tapered female opening could be mounted in conventional fashion. Each of the anterior and posterior sides of the proximal portion 40 of the stem 10 is provided with a flat surface as indicated at 60 in FIG. 1. Dovetail grooves 62, 64 are provided opening respectively downwardly into the flat surfaces 60. These dovetail grooves extend longitudinally in the proximal-distal direction and terminate with a closed end as indicated at 66 in FIG. 1. It will be seen that each of the illustrative enlarging portions is provided with a corresponding dovetail slide 68, 70 to be received respectively in the grooves 62, 64. Each of these dovetail slides 68, 70 terminates at its distal end with a distal portion to engage the distal end 66 of the grooves 62, 64. When each enlarging portion 14, 16, 18, 20, 22, 24, is mounted on the impaction stem 10 by means of the illustrative dovetail groove and slide arrangement, the upper surface 80 of the enlarging portion will be lying in the same plane as the upper surface 82 of the impaction stem.

Figure 2:
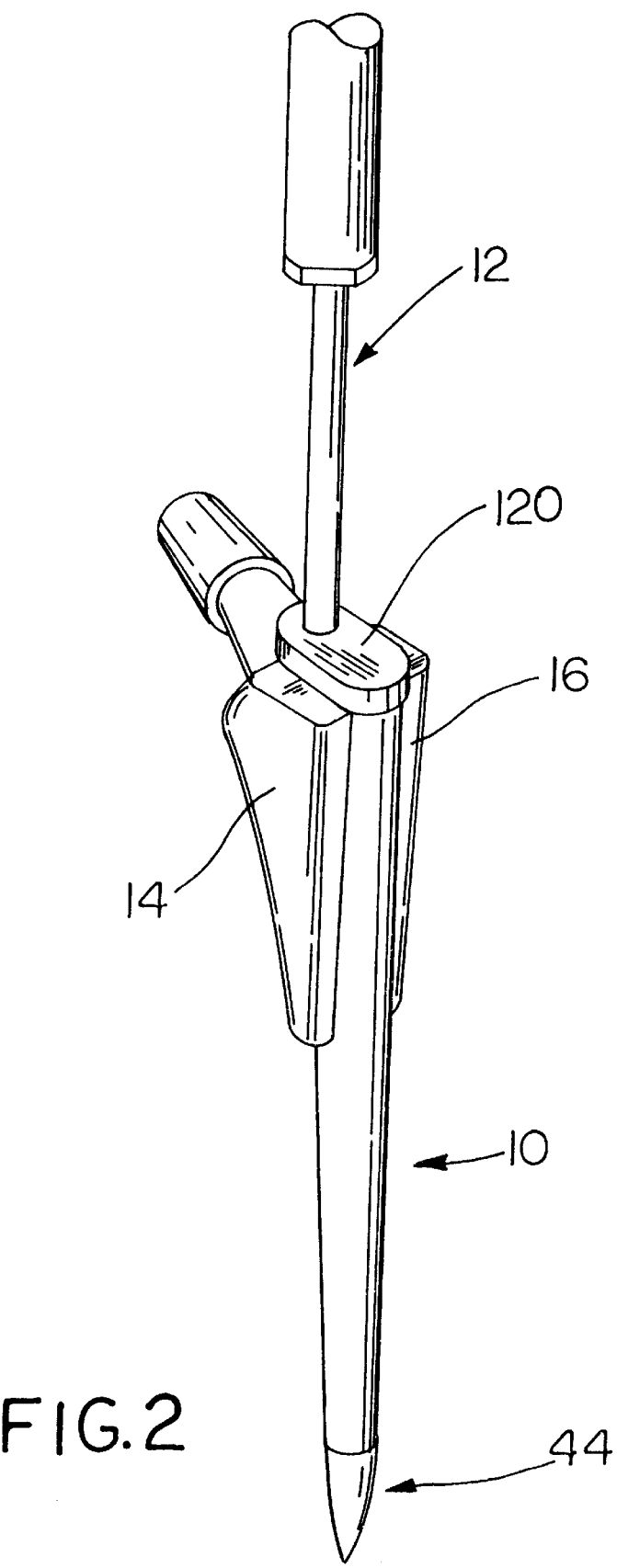
FIG. 2 is a view of the impaction instrument, assembled with a pair of enlarging portions, a stem extension, a handle, and a locking member.

The illustrative handle 12 is provided with a hand grip portion 100, a distally extending shaft portion 102 threaded at its distal end 104 as indicated in FIG. 1 to engage a threaded opening 110 in the upper surface 82 of the stem. This threaded distal end 104 extends through a locking member 120 which bridges across the upper surfaces of the enlarging portions and the stem 10 to lock the enlarging portions rigidly to the stem. Ideally, to prevent movement or rotation of locking member 120 during use, an integral male stud 92 fits into corresponding female opening 90 on upper surface 82. FIG. 2 illustrates this assembled configuration.

In the illustrative embodiment, therefore, the stem 10 and handle 12 are separable to facilitate the attachment of the enlarging portions 14, 16, 18, 20, 22, 24 selectively to the stem. It will be appreciated that other locking or attachment arrangements may be provided for rigidly attaching the enlarging portions to the stem 10. It will be appreciated that individual fasteners such as screws or other mechanical devices may be used to attach each enlarging portion to a side of the stem 10.

The illustrative flat surfaces 60 on the anterior and posterior sides of the proximal portion of stem 10 are provided for selectively mounting the pairs of enlarging portions to the stem beginning with the largest portions 14, 16, to perform the initial bone chip compaction. After bone chips are compacted to the wall of the cavity using the portions 14, 16, the largest portions are removed and replaced by the intermediate portions 18, 20 to do further compaction of bone chips against the layer which has been compacted by the largest portions 14, 16. Then, the intermediate portions 18, 20 are removed and the smallest portions 22, 24 are attached to the stem 10 to compact still another layer of bone chips against the wall of the cavity. Ultimately, even the smallest portions 22, 24 may be removed and the final compaction step made with the stem 10 to provide a cavity which is in the shape of the prosthetic stem to be implanted. It will be appreciated that the wedges are selected for shape and size based on the size of the femoral cavity. Wedges 14, 18, 22 may differ in size and shape from their counterparts 16, 20, 24. Selection of the appropriate sized largest wedges 14, 16, along with the appropriate length stem extension 44, provides an instrument which assures proper alignment when inserted into the femoral cavity.

The prosthetic stem to be implanted (not shown) is preferably of the type in which portions of its outer surface are covered with well known porous metal coatings. This combination of compacted bone chip walls and porous metal coating is provided to cause a rigid connection between the prosthetic stem and the femur by bone ingrowth, as well as to provide support to the proximal portion of the stem in cases of bone deficiency.

Still referring to FIGS. 1 and 2, and merely by way of illustrative example, a technique for internal bone compacting of the femur in cementless revision hip surgery will be described. It will be appreciated that revision surgery involves removal of an existing prosthetic stem carried in the proximal portion of the femur. Typically the previous stem has been cemented in place and the cement should be entirely removed from the femur cavity. Alternatively, a bone-ingrowth stem has been removed, thereby leaving an open area. Preferably, the femur will have an intact cortical shell in order to support the internal bone graft. Small cortical defects can be accommodated by the system to be described herein.

The following operative procedure may be used:
Templating.

Templates are made in accordance with well known templating procedures to provide anterior-posterior and lateral views of both femurs. Templates are then applied to the affected femur in order to determine an appropriate stem size. The templating is utilized to determine the appropriate prosthetic stem for replacement. Wedge templates are then applied to the lateral view of the affected femur to select the appropriate wedges 14, 16, 18, 20, 22, 24.

Femoral Preparation.

The previous implant and all cement and loose tissues are removed in a standard fashion. Similarly, the diaphyseal portion of the femur is prepared and reamed to the templated diameter using standard techniques.

Bone Compaction.

Using the templated impaction stem 10 as a base, the largest wedges 14 and 16 are attached to the impaction stem 10 using handle 12 and locking member 120. A stem attachment 44 may be used so that bone chips do not fall into the diaphysis during the procedure. The instrument is placed into the prepared femur so that the distal end 42 is in contact with the reamed diaphyseal portion of the femur, and graft material is added. Using vigorous blows to the handle 12, the graft material is compacted into the metaphyseal area. The instrument is then partially withdrawn, far enough to allow replacement of the largest wedges 14 and 16, but the stem attachment should remain in contact with the diaphysis.

Next, the largest wedges 14, 16 are replaced with the intermediate wedges 18, 20, additional graft material is inserted, and the material is compacted as before. The procedure is repeated with the smallest wedges 22, 24, and again using only the base impaction stem 10 itself for compaction. The handle 12 and locking member 120 may be removed to perform a trial reduction of the joint, as in standard techniques. Finally, handle 12 and locking member 120 are replaced in order to remove the impaction stem 10 from the femur. The resulting femoral cavity is then ready to receive the replacement prosthesis according to standard techniques.

I claim:

1. An instrument for compacting bone chips into a prepared metaphyseal portion of a femur to provide a cavity conformed to receive a femoral implant stem, the instrument comprising an impaction stem having a size and shape corresponding to the intended implant stem, said impaction stem having a proximal end and a distal end, a handle attached to the proximal end, and a plurality of enlarging portions to be attached to the impaction stem, said enlarging portions ranging in size from a largest size portion to a smallest size portion such that the bone compaction can be initiated with the largest size portion and repeated with successively smaller portions including the smallest portion to provide a cavity conformed to receive the implant stem.

2. The instrument of claim 1 in which the enlarging portions are wedge shaped and provided in pairs to be attached to the proximal end of the impaction stem, each wedge shaped portion tapering downwardly in size from its proximal end to its distal end.

3. The instrument of claim 2 in which each enlarging portion is provided with a connector portion and the impaction stem is provided with a mating connector portion.

4. The instrument of claim 3 in which the connector portions are mating male and female dovetail slide portions, one portion on each enlarging portion and one portion on the impaction stem.

5. The instrument of claim 4 in which the slide portions extend longitudinally in the proximal-to-distal direction of the stem and enlarging portions, and said handle includes a member for holding the slide portions in rigid contact when the handle is fastened to the impaction stem.

6. The instrument of claim 1, further comprising a stem extension which can be fixed to the distal end of the impaction stem.

7. An instrument for compacting graft material into a prepared metaphyseal portion of a femur to provide a cavity conformed to receive a femoral implant stem, the instrument comprising an impaction stem having a size and shape corresponding to the intended implant stem, said impaction stem having a proximal end and a distal end, a handle connected to the proximal end, and a plurality of enlarging portions to be attached to the impaction stem.

8. The instrument of claim 7, further comprising means for removably holding a pair of the enlarging portions in rigid contact with the proximal portion of the proximal end of the impaction stem.

9. A method for compacting bone chips into a prepared metaphyseal portion of a femur to receive a prosthesis stem comprising the steps of providing an impaction stem having a size and shape corresponding to the size and shape of the prosthesis stem to be installed in the femur, providing a plurality of enlarging portions to be attached to the impaction stem, the enlarging portions ranging in size from a largest size portion to a smallest size portion, filling the femur cavity with bone chips, starting with the largest size portion attached to the impaction stem, compacting a layer of bone chips within the cavity, and repeating the filling and compacting with successively smaller enlarging portions to obtain a cavity lined with compacted bone chips conformed to receive the prosthesis stem.

10. The method of claim 9 in which the impaction stem is elongated to extend in the proximal-distal direction and the enlarging portions are elongated to extend in the proximal-distal direction, each enlarging portion being wedge shaped to be larger at its proximal end than its distal end.

11. The method of claim 10 in which the enlarging portions are provided in pairs to be connected to opposite sides of the proximal end of the impaction stem.

12. The method of claim 11 in which the enlarging portions are attached to the impaction stem by rigid interlocking connector portions extending longitudinally and are held to the impaction stem by connecting a handle to the stem to lock the enlarging portions in place.

13. The method of claim 11 in which the size and shape of the largest pair of the enlarging portions is selected to provide, in combination with the impaction stem, an instrument which is proportioned and designed to provide proper alignment in the femoral tunnel.

14. A method for compacting bone chips into a prepared metaphyseal portion a femur to provide a cavity conformed to receive a femoral implant stem comprising the steps of providing an impaction stem having a size and shape corresponding to the size and shape of the femoral implant stem to be installed in the femur, said impaction stem having a proximal end and a distal end, providing a plurality of enlarging portions to be attached to the impaction stem, said enlarging portions ranging in size from a largest size portion to a smallest size portion, attaching the largest size enlarging portions to the proximal end of the impaction stem, placing the distal end of the impaction stem into the femur and advancing the impaction stem until the distal end contacts the diaphyseal portion of the femur, filling the prepared metaphyseal portion with graft material, compacting a layer of graft material within the cavity using vigorous blows, replacing the attached enlarging portions with smaller enlarging portions, repeating the filling and compacting steps using successively smaller enlarging portions to obtain a cavity lined with compacted graft material conformed to receive the femoral implant stem, and removing the impaction stem from the femur.

15. The method of claim 14 wherein the graft material comprises bone chips.

16. The method of claim 14 in which the distal portion of the impaction stem is only partially withdrawn from the femur when replacing the enlarging portions, and the impaction stem remains in contact with the diaphyseal portion until compaction is complete.

17. The method of claim 16, wherein the final step of filling and compacting is performed using the impaction instrument without any wedges attached thereto.

* * * * *